United States Patent [19]

Masumoto et al.

[11] 3,986,194
[45] Oct. 12, 1976

[54] MAGNETIC SEMICONDUCTOR DEVICE

[75] Inventors: Katashi Masumoto; Nobuyuki Koguchi, both of Tokyo, Japan

[73] Assignee: National Research Institute for Metals, Tokyo, Japan

[22] Filed: Aug. 11, 1975

[21] Appl. No.: 603,628

[30] Foreign Application Priority Data
Aug. 15, 1974  Japan............................ 49-92754

[52] U.S. Cl.................................. 357/18; 357/16; 357/27; 357/61; 331/94.5 H
[51] Int. Cl.² ................ H01S 33/19; H01L 29/161; H01L 27/22
[58] Field of Search .................. 357/18, 61, 16, 27; 331/94.5 H

[56] References Cited
UNITED STATES PATENTS

| 3,674,552 | 7/1972 | Heywang ............................ 117/217 |
| 3,818,328 | 6/1974 | Zinn .................................. 324/43 R |

Primary Examiner—Martin H. Edlow
Attorney, Agent, or Firm—Wenderoth, Lind & Ponack

[57] ABSTRACT

An injection-type laser light emitting semiconductor device comprising a main unit in the shape of a generally rectangular parallelepiped comprising a layer of a magnetic semiconductor for emitting laser light and at least one layer of semiconductor having the same crystal structure and substantially the same lattice constant as those of the magnetic semiconductor and also having a greater optical energy gap than that of the magnetic semiconductor, both end surface of the main unit perpendicular to the coalescing surface of the two layers serving as reflecting plates for the emission of laser light, and a pair of electrodes fixed ohmically to the under surface and top surface of the main unit. This device affords laser light whose wavelength varies over a relatively wide range according to changes in the oprical energy gap of the magnetic semiconductor as a result of changing the temperature and/or applied magnetic field.

11 Claims, 4 Drawing Figures

MAGNETIC SEMICONDUCTOR DEVICE

FIELD OF THE INVENTION

The invention relates to a magnetic semiconductor device for emitting laser light, and more specifically, to a magnetic semiconductor device which affords laser light whose wavelength can be varied easily over a wide range.

DESCRIPTION OF THE PRIOR ART

In order to apply semiconductor devices for emitting laser light to various uses such as communication and information processing, it is desired to change the wavelength of the laser light over a wide range. Various attempts have therefore been made to change the wavelength of the laser light on conventional laser-emitting semiconductor devices.

A semiconductor device using a GaAs compound is a typical example of the case where the wavelength of the laser light changes according to changes in temperature. The GaAs compound changes its optical energy gap according to changes in temperature, and therefore, the wavelength of the emitted laser light changes continuously (1.465 eV at 100° K, and 1.479 eV at 4.2° K. A semiconductor device using a PbSe compound is a typical example of the case where the wavelength of the emitted laser light changes with changes in pressure. The PbSe compound changes its optical energy gap according to changes in pressure, and therefore, the wavelength of the emitted laser light changes continuously (0.165 eV at 1 atmosphere, and 0.062 eV at 40,000 atmospheres). A typical example of the case where the wavelength of the emitted laser light changes according to changes in magnetic field is a semiconductor device using an InSb compound. The InSb compound does not emit laser light in the absence of magnetic field, but when the magnetic field changes, the wavelength of the emitted laser light changes continuously (at 17° K, 0.236 eV in a magnetic field of 28 KOe, and 0.245 eV in a magnetic field of 73 KOe).

With the conventional semiconductor devices, however, amounts of changes in the wavelength of the emitted laser light with changes in temperature, pressure or magnetic field are extremely small as described above, and in order to change the wavelength of the emitted laser light, the temperature, pressure or magnetic field needs to be drastically changed. This is an extremely difficult operation.

SUMMARY OF THE INVENTION

Accordingly, it is an object of this invention to provide an injection-type magnetic semiconductor device which emits laser light whose wavelength can be easily changed over a relatively wide range.

Another object of this invention is to provide an injection-type magnetic semiconductor device which emits laser light whose wavelength can be changed over a relatively wide range by changing its temperature and/or applied magnetic field.

We have now found that when a magnetic semiconductor is used of which optical energy gap changes over a relatively wide range with changes in temperature, especially in the vicinity of its magnetic transition temperature, and also with changes in applied magnetic field, there can be constructed an injection-type magnetic semiconductor device which emits laser light whose wavelength can be changed easily over a relatively wide range by changing its temperature and/or applied magnetic field.

According to this invention, there is provided an injection-type laser light emitting magnetic semiconductor device comprising a main unit in the shape of a generally rectangular parallelepiped comprising a layer of a magnetic semiconductor for emitting laser light and at least one layer of semiconductor having the same crystal structure and substantially the same lattice constant as those of the magnetic semiconductor and also having a greater optical energy gap than that of the magnetic semiconductor, both end surfaces of the main unit perpendicular to the coalescing surface of the two layers serving as reflecting plates for the emission of laser light, and a pair of electrodes fixed ohmically to the under surface and top surface of the main unit.

With the laser-emitting semiconductor device of this invention, the optical energy gap of the magnetic semiconductor changes over a relatively wide range with changes in temperature and/or applied magnetic field, and therefore, the wavelength of the emitted laser light changes over a relatively wide range.

DETAILED DESCRIPTION OF PREFERRED EMBODIMENTS

Figure 1:
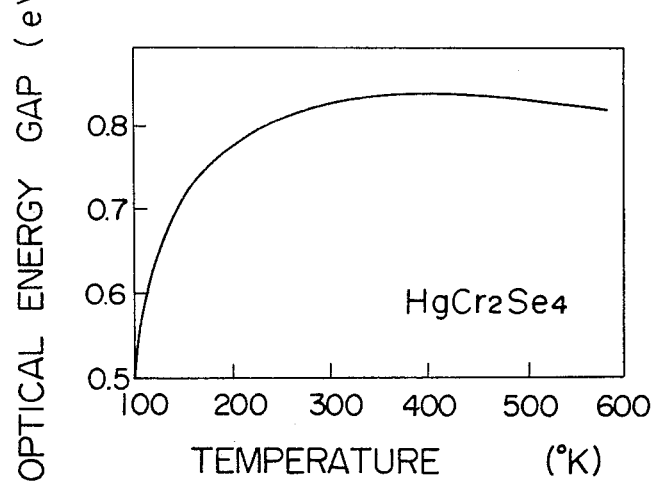
FIG. 1 is a diagram showing the relation between the optical energy gap and the temperature of $HgCr_2Se_4$.
Figure 2:
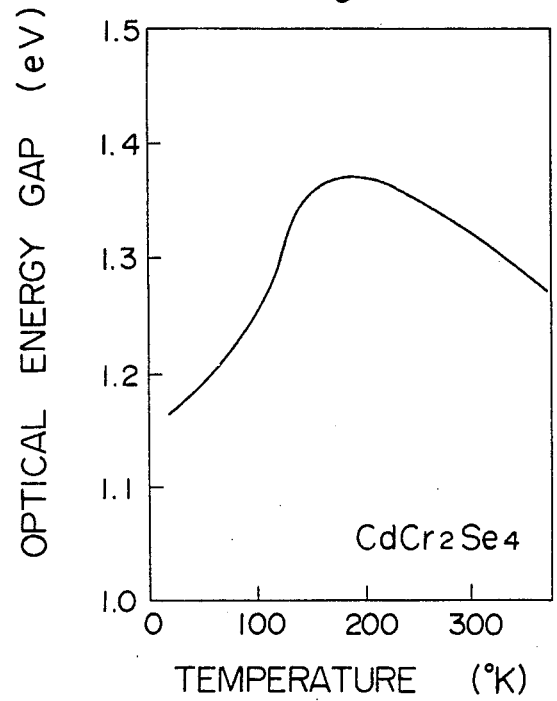
FIG. 2 is a diagram showing the relation between the optical energy gap and the temperature of $CdCr_2Se_4$.

Magnetic semiconductors, especially chalcogenide spinel ferromagnetic semiconductors such as $CdCr_2Se_4$, $HgCr_2Se_4$ or $HgCr_2S_4$, change their optical energy gap over a relatively wide range with changes in temperature, especially in the vicinity of their magnetic transition temperature, and also with changes in applied magnetic field. For example, $HgCr_2Se_4$ having a Curie point of 106° K exhibits the relation between optical energy gap and temperature as shown in FIG. 1. It has an optical energy gap of 0.77 eV at 200° K, and 0.50 eV at 100° K. When a magnetic field of 7.2 KOe is applied at 100° K, the optical energy gap decreases by as much as 0.042 eV. FIG. 2 shows the relation between the optical energy gap and the temperature of $CdCr_2Se_4$.

We have found that when a magnetic semiconductor, preferably a chalcogenide spinel ferromagnetic semiconductor, whose optical energy gap changes over a relatively wide range with changes in temperature and/or applied magnetic field and a semiconductor, for example, $CdIn_2S_4$, having the same crystal structure and substantially the same lattice constant as those of the magnetic semiconductor and a greater optical energy gap than that of the magnetic semiconductor are used, there can be constructed an injection-type laser-emitting magnetic semiconductor device of a single hetero or double hetero structure which emits laser light whose wavelength can be continuously changed over a relatively wide range, especially in the vicinity of its magnetic transition temperature, corresponding to changes in the optical energy gap of the magnetic semiconductor, by changing its temperature and/or applied magnetic field.

Figure 3:
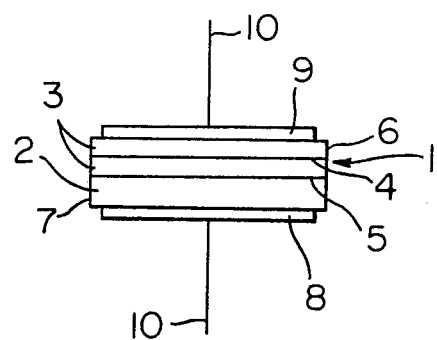
FIG. 3 is a side elevation of a magnetic semiconductor device of a single hetero structure in accordance with this invention.

Referring to FIG. 3, the injection-type laser-emitting magnetic semiconductor device of a single hetero structure will be described. The magnetic semiconductor device shown in FIG. 3 includes a main unit 1 in the shpe of a generally rectangular parallelepiped made up of a first layer 2 of, for example, an N-type semiconductor and a second layer of magnetic semiconductor formed on the first layer 2. The semiconductor in the first layer 2 has the same crystal structure and substantially the same lattice constant as those of the magnetic semiconductor in the second layer and a greater optical energy gap than that of the magnetic semiconductor in the second layer. $CdIn_2S_4$ is an example. The magnetic semiconductor in the second layer 3, preferably a chalcogenide spinel semiconductor such as $CdCr_2Se_4$, $HgCr_2Se_4$ or $HgCr_2S_4$, includes a P-N injection 4 substantially parallel to the coalescing surface between the first layer 2 and the second layer 3. The second layer 3 can be formed, for example, by growing a magnetic semiconductor having the same conductivity type as the semiconductor in the first layer 2, for example, the N-type, on the first layer 2 in a customary manner, and then forming a P-N junction 4 therein by a known diffusion technique.

Both end surfaces 6 and 7 which are parallel to each other and perpendicular to the coalescing surface 5 between the first layer 2 and the second layer 3 constitute reflecting plates for emitting laser light. These end surfaces may be cleaved or polished after mechanical cutting to form a mirror-like polished surface, or mirror-surface plated to form a reflecting mirror.

A pair of electrodes 8 and 9 are secured ohmically by a suitable method to the under surface and the top surface of the main unit which are parallel to the coalescing surface 5. A line 10 for supplying an electric current may be connected to the electrodes 8 and 9.

When a suitable pulse or D.C. current is passed through the main unit 1 by means of the electrodes 8 and 9 in the above-described magnetic semiconductor device, laser light having a wavelength corresponding to the optical energy gap of the magnetic semiconductor is emitted in a pulse form or continuous form from the magnetic semiconductor of the second layer 3 in a direction perpendicular to the end surfaces. When the temperature of the main body 1 and/or the magnetic field applied to it is changed, the wavelength of the emitted laser light continuously changes over a relatively wide range according to changes in the optical energy gap of the magnetic semiconductor.

Now, referring to FIG. 4, the injection-type laser-emitting magnetic semiconductor device of a double hetero structure in accordance with this invention will be described.

Figure 4:
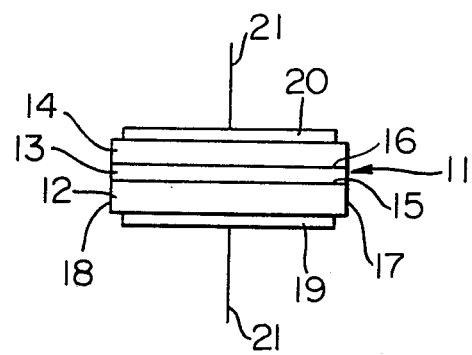
FIG. 4 is a side elevation of a magnetic semiconductor device of a double hetero structure in accordance with this invention.

The magnetic semiconductor device shown in FIG. 4 includes a main unit 11 in the shape of a generally rectangular parallelepiped made up of a first layer 12 of, for example, an N-type semiconductor, a second layer 13 of a magnetic semiconductor formed on the first layer 12, and a third layer 14 of, for example, a P-type semiconductor which is the same semiconductor as the layer 12 formed on the second layer 13. The semiconductors in the first layer 12 and the third layer 14 have the same crystal structure and substantially the same lattice constant as those of the magnetic semiconductor of the second layer 13, and a greater optical energy gap than that of the magnetic semiconductor of the second layer 13. An example is $CdIn_2S_4$. The semiconductor of the first layer 12 and the semiconductor of the third layer 14 must have mutually different conducting types. Preferably, the magnetic semiconductor of the second layer 13 is a chalcogenide spinel ferromagnetic semiconductor such as $CdCr_2Se_4$, $HgCr_2Se_4$ or $HgCr_2S_4$. The magnetic semiconductor of the second layer 13 may be of the P- or N-type, but preferably is an intrinsic semiconductor.

The main unit 11 described above can be formed, for example, by growing a magnetic semiconductor on the first layer 12 by a known method to form the second layer 13, and then growing a semiconductor on the second layer 13 to form a third layer 14.

Both end surfaces 17 and 18 of the main unit 11 which are parallel to each other and perpendicular to the coalescing surface 15 between the first layer 12 and the second layer 13 and the coalescing surface 16 between the second layer 13 and the third layer 14 constitute reflecting plates for emitting laser light. These end surfaces may be cleaved or polished after mechanical cutting to form a mirror-like polished surface, or mirror-surface plated to form a reflecting mirror.

A pair of electrodes 19 and 20 are secured ohmically to the under surface and the top surface of the main unit 11 which are parallel to the coalescing surfaces 15 and 16 by a suitable method. A line 21 may be connected to the electrodes 19 and 20 so as to pass an electric current through them.

When a suitable pulse or D.C. current is passed through the main unit 11 by means of the electrodes 19 and 20 of the magnetic semiconductor device, laser light having a wavelength corresponding to the optical energy gap of the magnetic semiconductor is emitted in a pulse form or continuous form from the magnetic semiconductor of the second layer 13 in a direction perpendicular to the end surfaces. By changing the temperature of the main unit 11 and/or the applied magnetic field applied to it, the wavelength of the emitted laser light changes continuously over a relatively wide range according to changes in the optical energy gap of the magnetic semiconductor.

The following Examples further illustrate the present invention.

EXAMPLE 1

1. One surface of a single crystal of an N-type $CdIn_2S_4$ semiconductor with a thickness of 1 mm was polished for mirror surface finish, and then etched. Then, an N-type $CdCr_2Se_4$ magnetic semiconductor having added thereto indium was grown onto the treated surface to a thickness of 5 $\mu$m by vapor phase growth.

2. Silver was vacuum-deposited to a thickness of about 1 micronmeter ($\mu$m) on the surface of the grown $CdCr_2Se_4$.

3. The product was then treated in a helium gas at 400° C. for 10 minutes thereby to form a P-N junction in the magnetic semiconductor.

4. Both end surfaces with a distance of 500 $\mu$m therebetween which were perpendicular to the coalescing surface and parallel to each other were formed by cutting, and then polished for mirror-like surface finish.

5. Both side surfaces having a suitable distance therebetween which were perpendicular to the coalescing surface and the two end surfaces were formed by cutting thereby to make a main unit in the shape of a rectangular parallelepiped.

6. Indium was vacuum-deposited on the under surface of the main unit and a lead line was fixed onto it. On the other hand, gold was vacuum-deposited on the top surface of the main unit, and a lead line was fixed onto it. Thus, an injection-type laser-emitting magnetic semiconductor device of a single hetero structure was constructed.

7. When an electric current of more than 1,000 A/cm$^2$ was passed through the magnetic semiconductor device, laser light having a wavelength corresponding to the optical energy gap of $CdCr_2Se_4$ was emitted from the N-type $CdCr_2Se_4$ in a direction perpendicular to the end surfaces. The wavelength of the emitted laser light changed with changes in the temperature of the semiconductor device and/or the magnetic field applied to it. For example, the wavelength was 0.01 μm (1.36 eV) at 200° K and 0.947 μm (1.31 eV) at 130° K. When a magnetic field of 8 KOe was applied in a direction pallarel to the P-N junction at 130° K, the wavelength was 0.954 μm (1.30 eV).

EXAMPLE 2

1. One surface of a single crystal of an N-type $CdIn_2S_4$ semiconductor with a thickness of 1 mm was polished for mirror-like surface finish, and etched. A P-type $HgCr_2Se_4$ magnetic semiconductor was grown on the treated surface to a thickness of 1 μm by vapor phase growth.

2. Then, a P-type $CdIn_2S_4$ semiconductor was grown to a thickness of about 2 μm on the surface of $HgCr_2Se_4$ by vapor phase growth.

3. Both end surfaces with a distance of 500 μm therebetween which were perpendicular to the coalescing surface and parallel to each other were formed by cutting, and then polished for mirror-like surface finish.

4. Both side surfaces having a suitable distance therebetween which were perpendicular to the coalescing surface and the two end surfaces were formed by cutting thereby to make a main unit in the shape of a rectangular parallelepiped.

5. Indium was vacuum-deposited on the under surface of the main unit and a lead line was fixed thereon. On the other hand, cadmium was vacuum-deposited on the top surface of the main unit and a lead line was fixed thereon. Thus, an injection-type laser-emitting magnetic semiconductor device of a double hetero structure was constructed.

6. When an electric current of more than 1,000 A/cm$^2$ was passed through the magnetic semiconductor device, laser light having a wavelength corresponding to the optical energy gap of $HgCr_2Se_4$ was emitted from the $HgCr_2Se_4$ in a direction perpendicular to the end surfaces. The wavelength of the emitted laset light changed according to changes in the temperature of the magnetic semiconductor device and/or the magnetic field applied to it. For example, the wavelength was 1.61 μm (0.77 eV) at 200° K., and 2.48 μm (0.50 eV) at 100° K. When a magnetic field of 7.2 KOe was applied at 100° K, the wavelength became 2.70 μm (0.46 eV).

What we claim is:

1. An injection-type laser light emitting magnetic semiconductor device comprising a main unit in the shape of a generally rectangular parallelepiped comprising a layer of a magnetic semiconductor for emitting laser light and at least one layer of semiconductor having the same crystal structure and substantially the same lattice constant as those of the magnetic semiconductor and also having a greater optical energy gap than that of the magnetic semiconductor, both end surfaces of the main unit perpendicular to the coalescing surface of the two layers serving as reflecting plates for the emission of laser light; and a pair of electrodes fixed ohmically to the under surface and the top surface of the main unit.

2. The semiconductor device of claim 1 wherein the magnetic semiconductor is a chalcogenide spinel ferromagnetic semiconductor.

3. The semiconductor device of claim 2 wherein the semiconductor of the second-mentioned layer is $CdIn_2S_4$.

4. An injection-type laser light emitting magnetic semiconductor device of a single hetero structure, comprising a main unit in the shape of a generally rectangular parallelepiped comprising a first layer of a semiconductor and a second layer of a magnetic semiconductor formed on the first layer and containing a P-N junction parallel to the coalescing surface between the first and second layers, the semiconductor of the first layer having the same crystal structure and substantially the same lattice constant as those of the magnetic semiconductor of the second layer and a greater optical energy gap than that of the magnetic semiconductor of the second layer, and the two end surfaces of the main unit perpendicular to the coalescing surface between the first and second layers serving as reflecting plates for the emission of laser light; and a pair of electrodes secured ohmically to the under surface and the top surface of the main unit which are parallel to the coalescing surface.

5. The semiconductor device of claim 4 wherein the magnetic semiconductor of the second layer is a chalcogenide spinel ferromagnetic semiconductor.

6. The semiconductor device of claim 5 wherein the semiconductor of the first layer is $CdIn_2S_4$.

7. An injection-type laser light emitting magnetic semiconductor device of a double hetero structure, comprising a main unit in the shape of a generally rectangular parallelepipied comprising a first layer of a semiconductor, a second layer of a magnetic semiconductor on the first layer and a third layer of a semiconductor which is the same semiconductor as the first layer on the second layer, the semiconductor of the first layer and the semiconductor of the third layer having different conducting-types from each other, and also having the same crystal structure and substantially the same lattice constant as those of the magnetic semiconductor of the second layer and a greater optical energy gap than that of the magnetic semiconductor, and both end surfaces of the main unit perpendicular to the coalescing surface between the first and second layers and the coalescing surface between the second and third layers serving as reflecting plates for the emission of laser light; and a pair of electrodes secured ohmically to the under surface and the top surface of the main unit which are parallel to the coalescing surfaces.

8. The semiconductor device of claim 7 wherein the magnetic semiconductor of the second layer is a chalcogenide spinel ferromagnetic semiconductor.

9. The semiconductor device of claim 8 wherein the semiconductor of the first layer and the semiconductor of the third layer are $CdIn_2S_4$.

10. The semiconductor device of claim 7 wherein the magnetic semiconductor of the second layer is an intrinsic semiconductor.

11. The semiconductor device of claim 10 wherein the magnetic semiconductor of the second layer is a chalcogenide spinel ferromagnetic semiconductor, and the semiconductors of the first and third layers are $CdIn_2S_4$.

* * * * *